(12) United States Patent
Rom (10) Patent No.: US 8,774,923 B2
(45) Date of Patent: Jul. 8, 2014

(54) OPTIMAL DEEP BRAIN STIMULATION THERAPY WITH Q LEARNING

(75) Inventor: Rami Rom, Zichron Yaacov (IL)

(73) Assignee: Sorin CRM SAS, Clamart (FR)

( * ) Notice: Subject to any disclaimer, the term of this patent is extended or adjusted under 35 U.S.C. 154(b) by 312 days.

(21) Appl. No.: 13/257,303

(22) PCT Filed: Mar. 18, 2010

(86) PCT No.: PCT/IL2010/000226
§ 371 (c)(1),
(2), (4) Date: Sep. 18, 2011

(87) PCT Pub. No.: WO2010/109448
PCT Pub. Date: Sep. 30, 2010

(65) Prior Publication Data
US 2012/0016435 A1      Jan. 19, 2012

Related U.S. Application Data

(60) Provisional application No. 61/162,303, filed on Mar. 22, 2009.

(51) Int. Cl.
*A61N 1/36* (2006.01)
(52) U.S. Cl.
USPC .............................................. 607/45; 607/62
(58) Field of Classification Search
CPC ... A61N 1/36; A61N 1/36014; A61N 1/3605; A61N 1/36082; A61N 1/05; A61B 5/0482; A61B 5/0488
USPC .............. 607/2, 3, 45, 62, 115–117; 600/544, 600/545
See application file for complete search history.

(56) References Cited

U.S. PATENT DOCUMENTS

| | | |
|---|---|---|
| 3,833,865 A | 9/1974 | Palmer |
| 5,692,907 A | 12/1997 | Glassel et al. |
| 5,800,471 A | 9/1998 | Baumann |

(Continued)

FOREIGN PATENT DOCUMENTS

| | | |
|---|---|---|
| WO | 01/95293 A2 | 12/2001 |
| WO | 2005/007075 A2 | 1/2005 |

(Continued)

OTHER PUBLICATIONS

International Search Report for PCT/IL2010/000226 issued Aug. 30, 2010 by European Patent Office as ISA.

(Continued)

*Primary Examiner* — Eric D. Bertram
*Assistant Examiner* — Pamela M Bays
(74) *Attorney, Agent, or Firm* — Simon Kahn; Chanoch Kahn (57) ABSTRACT

A closed loop Deep Brain Stimulation (DBS) system constituted of: a physiological sensor; a multi-electrode DBS lead; an adaptive control system in communication with the physiological sensor; and an implantable pulse generator (IPG) responsive to the adaptive control system, the adaptive control system comprising a learning module operable to learn to find the optimal stimulation parameters, classify and associate patient conditions responsive to the physiological sensor with optimal stimulation parameters in a plurality of patient conditions. The adaptive DBS device control system learns to deliver the optimal stimulation parameters based on Watkins and Dayan Q learning recursive formula, the closed loop adaptive DBS control system thus finds the optimal stimulation parameters online.

17 Claims, 7 Drawing Sheets

(56) References Cited

U.S. PATENT DOCUMENTS

| | | | |
|---|---|---|---|
| 6,016,449 A * | 1/2000 | Fischell et al. | 607/45 |
| 6,094,598 A * | 7/2000 | Elsberry et al. | 607/116 |
| 6,366,813 B1 | 4/2002 | DiLorenzo | |
| 6,459,929 B1 | 10/2002 | Hopper et al. | |
| 6,484,059 B2 | 11/2002 | Gielen | |
| 7,006,872 B2 | 2/2006 | Gielen et al. | |
| 7,209,787 B2 | 4/2007 | DiLorenzo | |
| 7,231,254 B2 | 6/2007 | DiLorenzo | |
| 7,242,984 B2 | 7/2007 | DiLorenzo | |
| 2003/0158587 A1* | 8/2003 | Esteller et al. | 607/45 |
| 2003/0204368 A1 | 10/2003 | Ertin et al. | |
| 2004/0138580 A1* | 7/2004 | Frei et al. | 600/544 |
| 2005/0202384 A1 | 9/2005 | DiCuccio et al. | |
| 2006/0235477 A1 | 10/2006 | Rom | |

FOREIGN PATENT DOCUMENTS

| | | |
|---|---|---|
| WO | 2006/017277 A2 | 2/2006 |
| WO | 2006/061822 A2 | 6/2006 |
| WO | 2008/010220 A2 | 1/2008 |
| WO | 2010/049931 A1 | 5/2010 |

OTHER PUBLICATIONS

Written Opinion of the International Searching Authority for PCT/IL2010/000226 issued Aug. 30, 2010 by European Patent Office as ISA.

Whinnett, Z.I. et al; "Haemodynamic Effects of Changes in AV and VV Delay in Cardiac Resynchronisation Therapy Show a Consistent Pattern: Analysis of Shape, Magnitude and Relative Importance of AV and VV Delay"; Published online by Heart 18, May 2006.

Watkins and Dayan; "Technical Note: Q-Learning"; published 1992 in Machine Learning, pp. 279-292, Boston, MA.

Rom et al; "Adaptive Cardiac Resynchronization Therapy Device: a Simulation Report"; published Nov. 2005, PACE, vol. 28, pp. 1168-1173.

Rom et al: "Adaptive Cardiac Resynchronization Therapy Device Based on Spiking Neurons Architecture ADN Reinforcement Learning Scheme"; Mar. 2, 2007, IEEE Transactions on Neural Networks, vol. 18, No. 2, pp. 542-550; IEEE New York, NY.

Kaelbling, L.P. et al; "Reinforcement Learning: A Survey"; Journal of Artificial Intelligence Research 4 (1996); pp. 237-285; AI Access Foundation and Morgan Kaufmann Publishers.

Whinnett, B.M. et al; "The Atrioventricular Delay of Cardiac Resynchronization Can Be Optimized Hemodynamically During Exercise and Predicted From Resting Measurements"; Journal of Heart Rhythm vol. 5, No. 3, Mar. 2008; pp. 378-386; Heart Rhythm Society.

Zuber, M. et al; "Comparison of Different Approaches for Optimization of Atrioventricular and Interventricular Delay in Biventricular Pacing"; Europace (2008) 10, pp. 367-373; European Society of Cardiology.

O'Donnell, D. et al: "Long-Term Variations in Optimal Programming of Cardiac Resynchronization Therapy Devices"; PACE, vol. 28, Jan. 2005, Supplement I, pp. S24-S26.

* cited by examiner

OPTIMAL DEEP BRAIN STIMULATION THERAPY WITH Q LEARNING

TECHNICAL FIELD

The invention relates generally to closed loop control systems, and in particular to a machine learning controller for a deep brain stimulation device. More specifically but not limited to, the invention deals with automatic optimization of Deep Brain Stimulation (DBS) therapy using a Q Learning scheme.

BACKGROUND ART

DBS is a therapy for movement disorders such as Parkinson Disease. DBS uses one or two surgically implanted medical devices called neurostimulators, similar to cardiac pacemakers, to deliver electrical stimulation to precisely targeted areas of the brain. One of two areas may be stimulated: either the subthalamic nucleus (STN) or the internal globus pallidus (GPi). These structures are deep within the brain and involved in motor control. A neurologist and a neuro-surgeon decide whether to target the STN or GPi. Stimulation of these areas appears to block the signals that cause the disabling motor symptoms of the disease. As a result, after DBS, many patients achieve greater control over their body movements. The entire system is implanted completely inside the body. Either one or two neurostimulators will be implanted to control symptoms which may affect both sides of the body. DBS leads offering a plurality of electrodes at different depths are commercially available, and allow for the delivery of stimulation using either one electrode or a combination of electrodes.

Presently, DBS therapy is primarily focused on the treatment of Parkinson's Disease, however DBS therapy is expected to expand to the treatment of migraine headaches, schizophrenia, depression, mania and other neurological disorders.

U.S. Pat. No. 6,484,059 issued Nov. 19, 2002 to Gielen et al, the entire contents of which is incorporated herein by reference, teaches an apparatus and method for optimal positioning of a deep brain stimulation electrode for treating movement disorders such as Parkinson's Disease (PD). The method uses two electrodes implanted in two different brain locations, preferably a DBS target such as the Globus Pallidum Internae (GPi) and a feedback target such as the motor cortex (MC). By stimulating both the DBS target and feedback target and observing the relevant patient body movement due to the motor cortex stimulation, the optimal DBS electrode location may be found.

However, after an optimal positioning of the DBS electrode is achieved, optimal stimulation parameters such as stimulation frequency, amplitudes, pulse width or patterns must be determined. Additionally, in the event that a DBS lead with a plurality of electrodes is provided, the appropriate electrode or combination of electrodes must be determined. Unfortunately, optimal stimulation patterns vary from patient to patient and generally are programmable parameters of an implantable pulse generator (IPG). Hence, in the prior art a clinician needs to adjust the stimulation parameters after implantation and perform regular follow up procedures. Such follow up procedures are both costly and inconvenient.

U.S. Pat. No. 7,006,872 issued Feb. 28, 2006 to Gielen et al, the entire contents of which is incorporated herein by reference, teaches a system and method for predicting the likelihood of occurrence of an impending neurological episode. Electrical stimuli are delivered to a structure of the brain. Response field potentials evoked by the stimuli are sensed. Analysis of these field potentials allows for predictions as to the occurrence of an impending, but not yet occurring, neurological disorder. In one example, a measurement of change in response pulses is used to determine a level of interconnectivity in the structures of the brain. The level of functional interconnectivity is used in predicting the occurrence of the neurological event. An example of such a neurological event includes an epileptic seizure. In summary, from the changes in the response of the brain activity to the two stimulations a decision can be made regarding an impending epilepsy episode and an appropriate stimulation therapy can be delivered.

Gielen, in the above mentioned U.S. patent, further teaches that the threshold value defining a likely neurological episode may be a self learning process. The pulse therapy is defined by a clinician at time of implantation and is updated as needed. The sensed signals may be stored on a memory for retrieval by the clinician for therapy assessment. Treatment is set by a clinician, and only the triggering mechanism is learned.

U.S. Pat. No. 7,231,254 issued Jun. 12, 2007 to Dilorenzo, the entire contents of which is incorporated herein by reference, teaches a closed loop system for neuromodulation in general and more specifically also a closed loop deep brain stimulation control system for Parkinson patients. The closed loop controllers of Dilorenzo deliver neuromodulation responsive to treatment parameters derived from a neural response to previously delivered neural modulation signals sensed by one or more sensors. However Dilorenzo does not describe using a machine learning scheme to find optimal stimulation parameters derived such that the control system will achieve the optimal stimulation therapy on line and without prior knowledge of patient characteristics and in different patient daily life activities.

Thus, according to the prior art the complicated task of finding the optimal lead position, and/or combination of leads, in implantation and optimizing the IPG stimulation parameters are done manually by the clinician during implantation and patient follow up and with no systematic method to ensure that optimal therapy will be delivered.

Q-learning (QL) is a reinforcement learning technique that works by learning an action-value function that gives the expected utility of taking a given action in a given state and following a fixed policy thereafter. One of the strengths of Q-learning is that it is able to compare the expected utility of the available actions without requiring a model of the environment. Watkins and Dayan in an article entitled "Q Learning", published 1992 in Machine Learning 8, 279-292, 1992, showed that online solution of a QL recursive formula is guaranteed to converge to the optimal policy in a model free reinforcement learning problem.

There is therefore a long felt need to develop a systematic closed loop DBS device control system that will achieve optimal stimulation therapy and wherein parameters for appropriate stimulation therapy are controlled automatically by a machine learning, module without requiring constant manual patient follow up.

SUMMARY OF THE INVENTION

Accordingly, it is a principal object of the present invention to overcome at least some of the disadvantages of prior art open loop DBS devices. This is provided in the present invention by a machine learning based control system that learns to deliver the optimal stimulation to the patient based on a reinforcement learning (RL) scheme that learns online and without need of a prior model of patient response. The present invention preferably utilizes a model free Q Learning scheme and operates in a plurality of operational modes with a built in preference to operate in an adaptive Q learning (QL) mode. In particular, the closed loop DBS control system finds the optimal stimulation frequency, stimulation electrodes and amplitude using the Q Learning scheme, and learns to associate the learned optimal stimulation parameters with temporal patterns of brain activity or other invasive or non-invasive sensors. Such a machine learning based control system is particularly useful for the development of a closed loop DBS system responsive to a brain electrical activity sensor or other invasive or non-invasive sensor.

The present embodiments provide for a closed loop Deep Brain Stimulation (DBS) system comprising: a physiological sensor, the physiological sensor comprising at least one of a brain activity sensor and a mechanical body motion sensor; an adaptive control system in communication with the physiological sensor; and an implantable pulse generator (IPG), the IPG arranged to provide pulses selectively to one or more electrodes of a multi-electrode DBS lead responsive to stimulation parameters provided by the adaptive control system, the adaptive control system comprising: a learning module arranged to determine stimulation parameters to be output to the IPG responsive to feedback received from the physiological sensor wherein the stimulation parameters comprise a selection of a particular set of the one or more electrodes of the multi-electrode DBS lead; and a deterministic algorithmic module arranged to maintain safety limits for determined stimulation parameters provided to the IPG.

In one further embodiment the stimulation parameters additionally comprise at least one of a stimulation frequency, amplitude, a pulse width, and time sequences. In another further embodiment the stimulation parameters additionally comprise at least one of a stimulation frequency, amplitude, a pulse width, and time sequences.

In one further embodiment the adaptive control system is arranged to operate in a plurality of states, the states comprising: a non-adaptive state wherein the adaptive control system controls the IPG to deliver stimulation in accordance with received input stimulation parameters; an adaptive GA learning state wherein the input stimulation parameters are modified by the adaptive control system and optimal parameters for varying patient conditions are learned responsive to feedback received from the physiological sensor, the learning comprising storing reward function values responsive to the modified stimulation parameters and resultant inputs from the physiological sensor in a QL look up table; and an adaptive QL state in which the adaptive control system operates the IPG alternately responsive to inputs from the physiologic sensor and inputs stored in the QL look up table, the alternate selection responsive to a probabilistic scheme.

In one yet further embodiment the closed loop DBS system additionally comprises an external programmer in communication with the adaptive control system, the received input stimulation parameters provided via the external programmer. In one yet additional further embodiment the adaptive control system additionally comprises: an adaptive FAIL QL state in which a pattern recognition sigmoid neural network is operative to converge back to the received input stimulation parameters when a change of state occurs and the pattern recognition networks fails to associate the new pattern with an optimal solution.

In one yet further embodiment the adaptive control system exhibits a built in priority to operate in the adaptive QL state. In one yet further embodiment the adaptive control system transits from the adaptive QL state to one of the adaptive GA learning state and non-adaptive state responsive to one of: a pre-defined failure; and an override input.

In one further embodiment the physiological sensor comprises at least one of an accelerometer, a tremor sensor and a rigidity sensor. In another further embodiment the physiological sensor comprises at least one of a brain activity sensor and a mechanical body motion sensor.

In one further embodiment the physiological sensor is invasive. In one further embodiment the physiological sensor is non-invasive. In another further embodiment the adaptive control system comprises a neural network processor.

Independently, the present embodiments additionally provide for a method for deep brain stimulation (DBS) delivered to a patient in a closed loop system, the method comprising: providing a physiological sensor; providing a multi-electrode DBS lead; determining stimulation parameters to be provided via the provided multi-electrode DBS lead responsive to feedback received from the provided physiological sensor wherein the stimulation parameters comprise a selection of a particular set of the one or more electrodes of the provided multi-electrode DBS lead; and maintaining safety limits for the stimulation parameters provided to the multi-electrode DBS lead.

In one further embodiment the determining stimulation parameters comprises: delivering brain stimulation via the provided multi-electrode DBS lead according to programmed stimulation parameters; machine learning the programmed stimulation parameters; switching to an adaptive GA learning state when the machine learning converges; modifying the programmed stimulation parameters thereby learning optimal stimulation parameters responsive to feedback from the provided physiological sensor; storing reward function values responsive to the modified stimulation parameters and resultant inputs from the physiological sensor in a QL look up table; and in the event that the learning optimal stimulation parameters converges within predetermined parameters, switching to an adaptive QL state in which brain stimulation is provided via the provided multi-electrode DBS lead alternately responsive to inputs from the physiologic sensor and inputs stored in the QL look up table, the alternate selection responsive to a probabilistic scheme.

In one yet further embodiment the method additionally comprises receiving the programmed parameters, the programmed stimulation parameters comprising at least one of a stimulation frequency, amplitude, a pulse width, a particular electrode of the multi-electrode DBS lead and a time sequence. In another yet additional further embodiment the method additionally comprises: converging back to the received input stimulation parameters when a change of state occurs which is not associated with the optimal solution.

In one yet further embodiment the method exhibits a built in priority to operate in the adaptive QL state. In another yet additional further embodiment the method additionally comprises transiting from the adaptive QL state to one of the adaptive GA state and non-adaptive state responsive to one of: a pre-defined failure; and an override input.

In one further embodiment the provided physiological sensor comprises at least one of a brain activity sensor and a mechanical body motion sensor. In any further embodiment the provided physiological sensor comprises at least one of an accelerometer, a tremor sensor and a rigidity sensor.

Advantageously, the closed loop DBS control system overcomes the difficulties of sub-optimal DBS therapy due to both sub-optimal DBS lead positioning and the lack of systematic patient follow-up routine aimed at optimizing the DBS device stimulation parameters manually after a DBS lead is implanted.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

The present embodiments enable a closed loop DBS system to deliver the optimal physiologic therapy to PD patients. In particular, the closed loop DBS control system learns to optimize dynamically and to deliver therapy responsive to one or more of a brain activity sensor and a mechanical body motion sensor in a closed loop machine learning technique.

In particular, the present closed loop DBS control system utilizes Watkins and Dayan, "Q Learning", described above, which converges to the optimal policy in a model free reinforcement learning problem, to provide an agent IPG that learns the optimal stimulation parameters for an implanted DBS device implanted in a patient and hence delivers optimal DBS therapy.

As described above, advantageously, the closed loop DBS control system overcomes the difficulties of sub-optimal DBS therapy due to both sub-optimal DBS lead positioning and the lack of systematic patient follow-up routine aimed at optimizing the DBS device stimulation parameters manually after a DBS lead is implanted.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1:
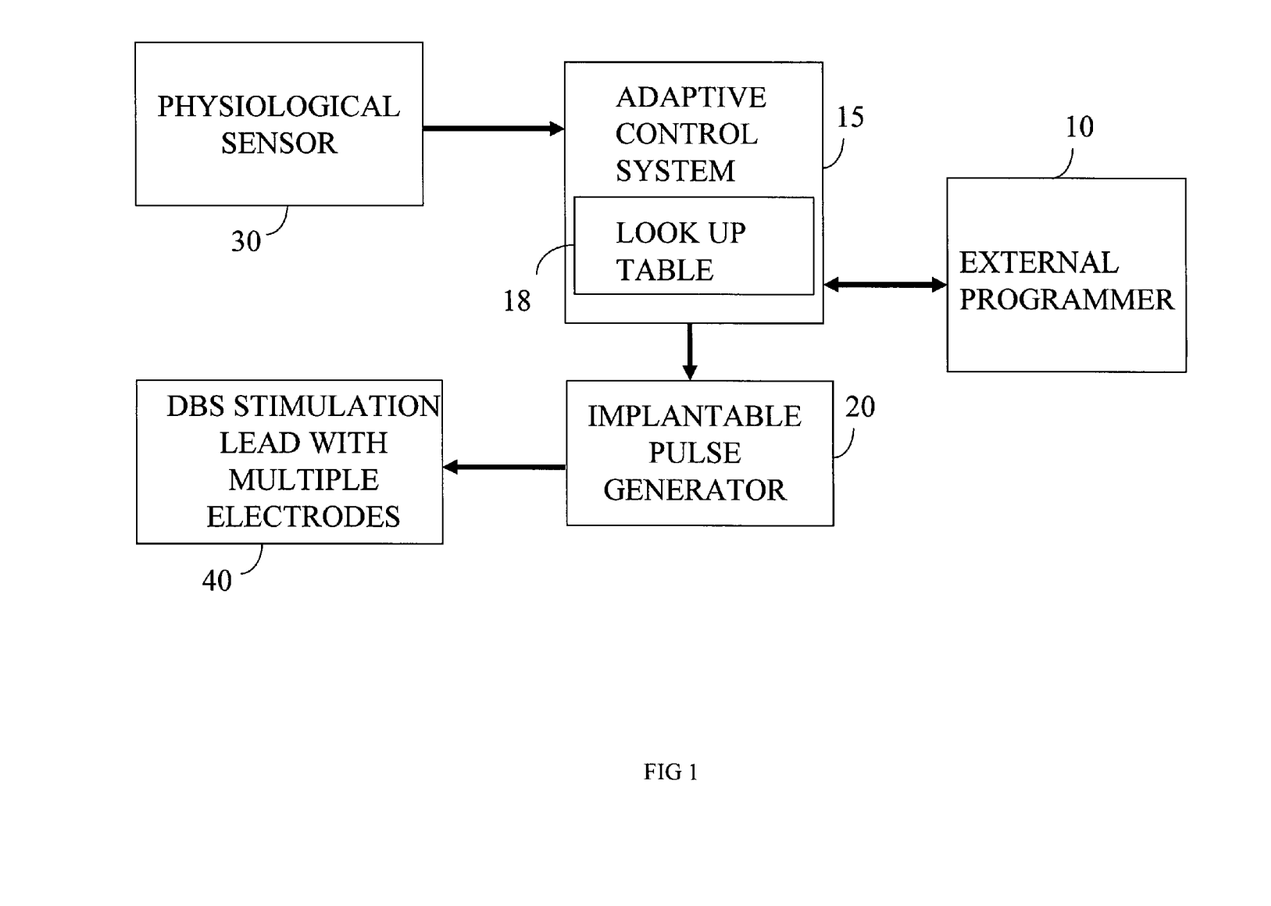
FIG. 1 illustrates an exemplary embodiment of a closed loop DBS system comprising: an adaptive control system; an IPG responsive to the adaptive control system; at least one of a brain electrical activity sensor and a mechanical body motion sensor; a DBS lead responsive to the IPG comprising a plurality of electrodes; and an external programmer.

FIG. 1 illustrates an exemplary embodiment of a closed loop DBS system comprising: an external programmer 10; an adaptive control system 15 comprising a QL look up table 18; an IPG 20; a physiological sensor 30, comprising at least one of a brain activity sensor and/or mechanical body motion sensor; and a multi-electrode DBS lead 40 that allows for dynamic selection of the stimulation delivery electrode. In one embodiment physiological sensor 30 is constituted of a brain activity sensor, and in another embodiment physiological sensor 30 is constituted of a mechanical body motion sensor positioned to sense physical uncontrolled movement. The mechanical body motion sensor preferably comprises an accelerometer, tremor sensor or rigidity sensor. In one embodiment physiological sensor 30 is implanted within a patient body, and in another embodiment physiological sensor 30 is worn externally to a patient body.

Multi-electrode DBS lead 40 is implanted in the patient body allowing for dynamic selection of the stimulation delivery electrode and is in communication with IPG 20. IPG 20 is responsive to an output of adaptive control system 15. Adaptive control system 15 is in communication with physiological sensor 30. Adaptive control system 15 is further in communication with external programmer 10, the communication being one of an RF channel, magnetic channel, or other manual input known to those skilled in the art. In an exemplary embodiment external programmer 10 comprises a display panel, operative to give a visual indication of the changing IPG stimulation parameters output by IPG 20 and the response to deep brain stimulation as detected by physiological sensor 30. External programmer 10 further provides an interface for setting the defined parameters for the non-adaptive operational state of adaptive control system 15 described further hereinto below. Adaptive control system 15 preferably comprises a spiking neural network and a temporal pattern neural network.

In operation, adaptive control system 15 controls IPG 20 to deliver DBS therapy via a specific electrode, or a set of electrodes, of multi-electrode DBS lead 40, the specific electrode, or set of electrodes, selected in accordance with the operational states of adaptive control system 15. In particular in a first state, known as the non-adaptive state, adaptive control system 15 operates IPG 20 responsive to input parameters received from external programmer 10 and further receives sensed data regarding brain activity data from physiological sensor 30.

Adaptive control system 15 performs a machine learning algorithm and switches between four operating states that will be described further hereinto below. The machine learning methods, pattern recognition neural network and operating modes are similar to those described in international patent application publication S/N WO 2005/007075 published Jan. 25, 2005 to Rom, entitled "Adaptive Resynchronization Therapy System", the entire contents of which is incorporated herein by reference, and S/N PCT/IL2009/001009 to Rom, entitled "Optimal Cardiac Pacing With Q Learning", the entire contents of which is incorporated herein by reference.

Adaptive control system 15 receives stimulation parameters from the clinician, through external programmer 10, and in the non-adaptive state, operates IPG 20 in an open loop DBS system known to the prior art. Adaptive control system 15 is further operable, responsive to a machine learning algorithm to switch to a second state, known as the adaptive gradient ascent (GA) state, in which adaptive control system 15 modifies the stimulation parameter using a systematic trial and error GA scheme in order to maximize a response function derivative calculated from the output of physiological sensor 30. Adaptive control system 15 is further operable, upon convergence of the machine learning algorithm, to switch to a third state, known as the adaptive QL DBS state, in which adaptive control system 15 controls IPG 20 to deliver DBS therapy via multi-electrode DBS lead 40 responsive alternately to the output of physiological sensor 30 and its own predictions based on Watkins and Dayan Q Learning recursive formula described below. Adaptive control system 15 is further operable, when a pre-defined failure occurs, to switch to a fourth state, known as the FAIL QL state. The four operational states are described further below and in FIG. 3.

Figure 2:
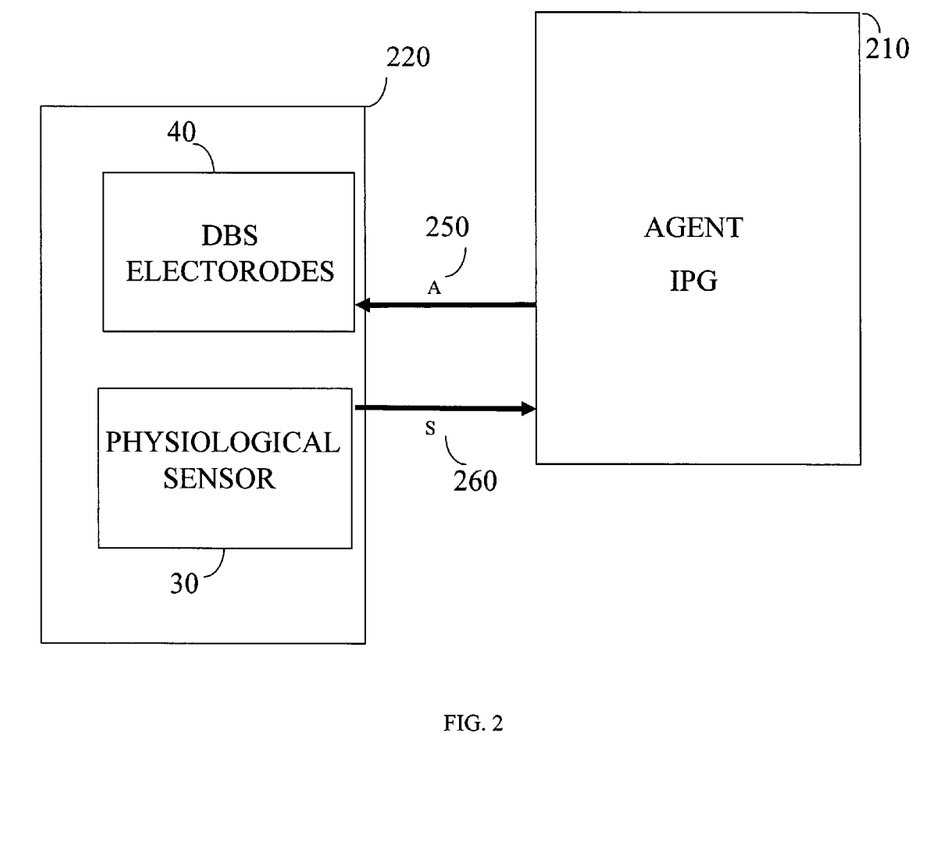
FIG. 2 illustrates an exemplary embodiment of a reinforcement learning problem adopted to brain stimulation.

FIG. 2 illustrates a Reinforcement Learning (RL) problem adaptation to DBS. An agent IPG, 210, learns optimal behavior through trial-and-error interactions with a dynamic environment of the patient brain or body responses, 220. The dynamic environment 220 comprises multi-electrode DBS lead 40 and physiological sensor 30, as described above in relation to FIG. 1. In a preferred embodiment agent IPG 210 comprises adaptive control system 15 and IPG 20, both of FIG. 1. In the standard reinforcement learning model "Reinforcement Learning: A Survey", Leslie P. Kaebling, Michael L. Littman and Andrew W. Moore, Journal of Artificial Intelligence Research 4, 237-285, 1996, the entire contents of which is incorporated herein by reference, the agent is connected to its environment via perception and action. Agent IPG 210 receives as an input the patient current state, denoted S, of dynamic environment 220 from physiological sensor 30 via a connection 260. Agent IPG 210 then chooses the stimulation frequency, amplitude or active lead as its possible actions, denoted A, to generate as output for delivery over connection 250 to DBS electrodes 240. Agent IPG 210 actions A (stimulation) changes the state of the brain electrical or patient mechanical response (the environment state), and the value of this change is calculated by agent IPG 210 from the sensor input received via connection 260 as a scalar reinforcement signal. The task of agent IPG 210 is to choose online the actions A (stimulation parameters) that tend to increase the long run sum of values of the scalar reinforcement signal S. It can learn to do this over time by systematic trial and error, guided by a variety of RL algorithms. Preferably, the Watkins and Dayan Q Learning recursive formula explained below is implemented.

Watkins and Dayan Q learning recursive formula is—

$$Q(S,A)=Q(S,A)+\alpha(R(S,A)+\gamma Q_{maxA}(S,A)-Q(S,A)) \quad \text{EQ. 1}$$

Where:
A is the agent action;
S is the environment state;
Q(S,A) is the expected discounted reinforcement of taking action A in state S table;
R(S,A) is the immediate reward response of the environment, which in a non-limiting embodiment is a derivative of the mechanical sensor signal;
$\alpha$ is a small learning rate factor ($\alpha \ll 1$);
$\gamma$ is a discount factor (smaller then 1); and
$Q_{maxA}$ (S,A) is the maximal Q value associated with the best action A at a given state S. After convergence of the Watkins and Dayan Q learning recursive formula, the learned Q(S,A) stored by adaptive control system 15 as QL lookup table 18 converges to the optimal policy, i.e. the optimal action A at a given state S out of the possible set of actions will have maximum Q value.

In the exemplary embodiment of closed loop DBS, as shown in FIG. 1 and FIG. 2, there are stimulation frequency, amplitude, and active electrode selection, parameters that can be optimized online. Hence the Q table is calculated for each configuration of frequency, amplitude, and selected active electrode and for each value the possible actions are an increase or a decrease in the next time period. In particular:

$$Q(S,A)=Q(S,\omega,A,P) \quad \text{EQ. 2}$$

Where:
$\omega$ is the IPG stimulation frequency;
A is the IPG stimulation amplitude;
P is the IPG stimulation electrode identifier in multi-electrode DBS lead 40;
S is the patient state as seen through physiological sensor 30; and
Q(S, $\omega$, A, P) is the expected discounted reinforcement calculated lookup table of stimulating with $\omega$, A, P parameters. $Q_{max\,\omega,A,P}$ (S, $\omega$, A, P) denotes the Q value with the optimal $\omega$, A, P values. In the present embodiments the Watkins and Dayan Q Learning recursive formula is calculated online by adaptive control system 15 and stored in lookup table 18. In parallel, the calculated lookup table values are used to replace the sensed gradients responsive to inputs received from physiological sensor 30 in a probabilistic replacement scheme that depends on the calculated Q values, as described above in relation to EQ. 1 and EQ. 2. The Q values are seen as a confidence value of a prediction of the QL scheme and when for a given change (agent action) in a stimulation parameter the difference between the QL lookup table value compared to other possible changes is large, the reinforcement signal forwarded to an integrate and fire (I&F) neurons synaptic adjustments scheme is replaced with the QL look up table difference and not the sensed gradient from physiological sensor 30. The probabilistic replacement mechanism means that when a high confidence in a stimulation parameter change is obtained the system ignores the input gradient value from physiological sensor 30 and operates according to its own prediction as accumulated in QL lookup table 18. This mechanism allows the system to learn online its environment responses to stimulation with different values and to operate optimally according to the accumulated experience.

As indicated above, Watkins and Dayan have demonstrated in "Q Learning", published in Machine Learning 8, 279-292, 1992, that by solving the Q learning recursive formula online the agent learns the optimal policy in a model free reinforcement learning problem with probability of 1 when the actions space is visited enough times online, meaning that exploration of the action space is sufficient. The advantage of Watkins and Dayan Q-learning adapted for an agent IPG here is that the DBS therapy parameters obtained by solving the recursive formula converge to the optimal policy, i.e. the optimal stimulation parameters that will give maximum future performance and without any prior knowledge of the patient responses.

Preferably, adaptive control system 15 comprises a neural network module (not shown) operating as a slave processor to a deterministic algorithmic module (not shown) as described in U.S. Patent Application Publication S/N 2006/0235477 published Oct. 19, 2006 to ROM and entitled "Adaptive Resynchronization Therapy System", the entire contents of which is incorporated herein by reference. In particular, adaptive control system 15 thus comprises the neural network module and the deterministic algorithmic module, the deterministic algorithmic module receiving parameters from the neural network module, supervising the parameters, and provided the parameters are within predetermined deterministic boundaries, controlling IPG 20 to deliver DBS therapy responsive to the neural network module.

A responder curve, similar to a responder curve taught in International Application Publication S/N WO2006/061822 published Jun. 15, 2006 to ROM and entitled "OPTIMIZING AND MONITORING ADAPTIVE CARDIAC RESYNCHRONIZATION THERAPY DEVICES", the entire contents of which is incorporated herein by reference, is preferably further used to determine if an effective and optimal stimulation site is achieved during the implantation, and if the clinician is not satisfied with the response curve obtained, the clinician may further change the lead position during brain surgery.

Furthermore, multi-electrode DBS lead 40 in combination with the machine learning scheme as described herein can deliver DBS through a specific electrode of multi-electrode DBS lead 40, the selection of the specific electrode being accomplished responsive to the machine learning scheme, resulting in an optimal responder curve. Since the Globus Pallidum Internae (GPi) and the subthalamic nucleus (STN) are small DBS targets, switching the stimulation electrode by 1 to 10 mm or more along the implanted multi-electrode lead will be significant. Hence, the combination of a multi-electrode DBS lead 40 and a machine learning scheme of the present invention may ease finding the optimal site for the implanted DBS lead significantly during the surgery and improve the overall delivered therapy. As indicated above, a plurality of electrodes may be selected without exceeding the scope.

Figure 3:
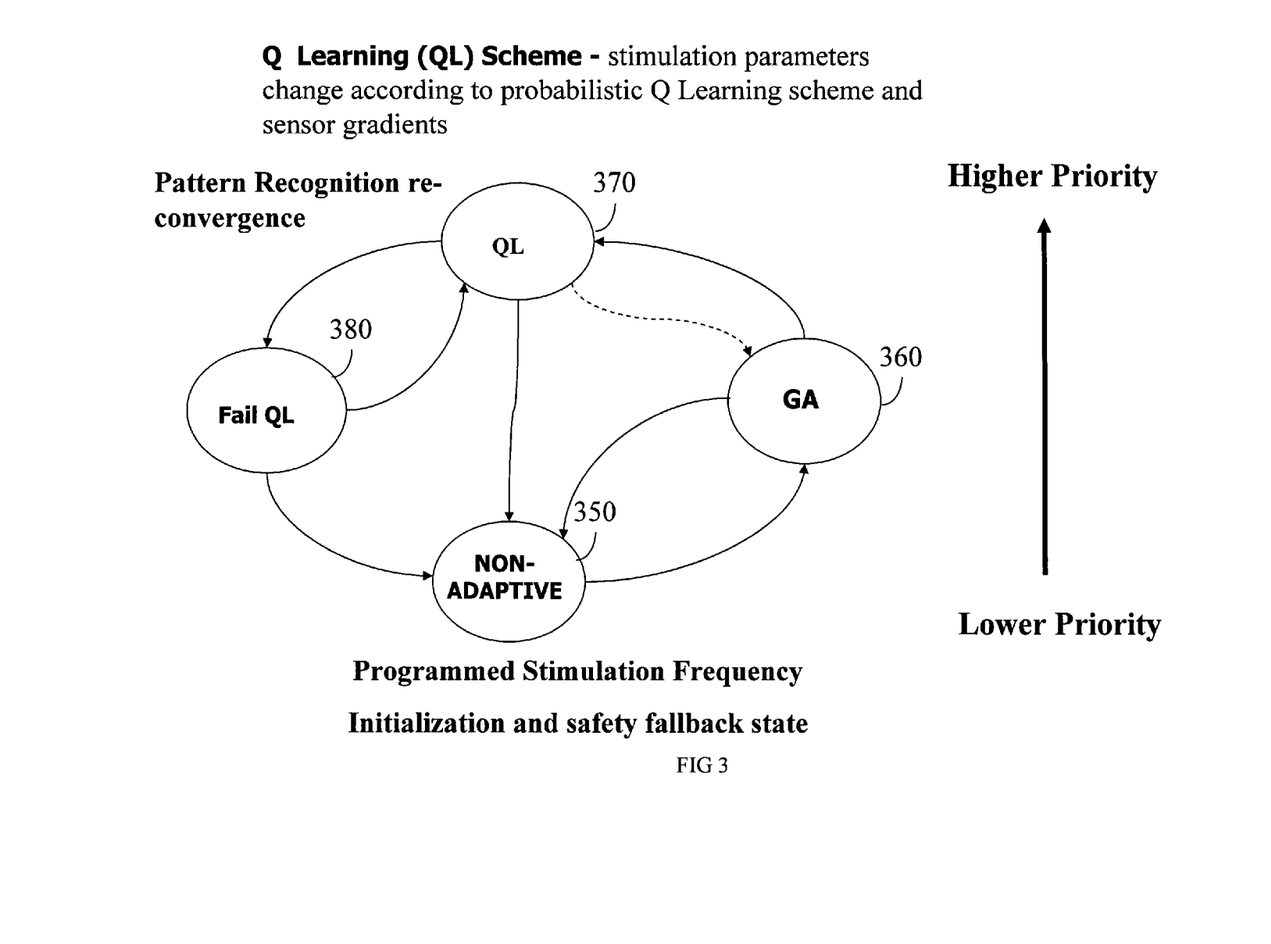
FIG. 3 illustrates an exemplary embodiment of a high level block diagram of the states of the adaptive control system of FIG. 1, exhibiting four states of operation with a built in preference for an adaptive QL state.

FIG. 3 illustrates an exemplary embodiment of a high level block diagram of states of adaptive control system 15 of FIG. 1, exhibiting four states of operation, in particular non-adaptive state 350, adaptive GA state 360, adaptive QL state 370, also known as adaptive GRL DBS state, and FAIL QL state 380. In non-adaptive state 350, adaptive control system 15 delivers stimulation via IPG 20 responsive to programmed stimulation parameters received via external programmer 10, the programmed stimulation parameters being supplied by a clinician. Adaptive control system 15, operating in non-adaptive state 350, further learns to associate the temporal pattern received from physiological sensor 30 with the stimulation parameters programmed by the clinician via external programmer 10. Adaptive control system 15 exhibits a higher priority to be in adaptive GA state 360 than in non-adaptive state 350, and a further higher priority to be in adaptive QL state 370.

In particular, adaptive control system 15 performs an integrate-and-fire (I&F) neurons learning scheme similar to the learning schemes taught in International Patent Application Publication WO 2005/007075 referenced above for implanted adaptive cardiac resynchronization therapy (CRT) pacemaker devices.

Upon convergence of the I&F neurons network of non-adaptive state 350, i.e. convergence of the spiking neural network of adaptive control system 15, adaptive control system 15 switches to adaptive GA state 360, in which adaptive control system 15 modifies the stimulation parameters responsive to the gradients of the output of physiological sensor 30 in order to maximize the absolute value of a response function derivative calculated from the output of physiological sensor 30. Preferably, the change in state is communicated to external programmer 10 for display.

Adaptive control system 15 is further operable, upon further convergence of the machine learning algorithm of adaptive GA state 360, in particular when the temporal pattern neural network matches the output of the spiking neural network within predetermined parameters, to switch to adaptive QL state 370, in which adaptive control system 15 delivers DBS therapy via IPG 20 alternately responsive to the inputs from physiological sensor 30 and to its own prediction based on the Q Learning lookup table calculated online according to Eq. 1 above, the selection in accordance with a probabilistic scheme. The above mentioned temporal patterns neural network learns to map the input pattern with the learned optimal values and when a change is detected in the input pattern a transition to FAIL QL state 380 will occur.

A clinician may override adaptive control system 15 at any time via external programmer 10, and in response adaptive control system 15 switches to a lower priority state, for example the initial non-adaptive state. Adaptive control system 15 is preferably further operative in the adaptive QL state to display the input received from physiological sensor 30 and the parameters controlling IPG 20 via external programmer 10.

Preferably, adaptive control system 15 is constituted of a neural network module operating as a slave processor to a deterministic algorithmic module as described in U.S. Patent Application Publication S/N 2006/0235477, referenced above. Thus, in adaptive GA state 360, adaptive QL state 370 and FAIL QL state 380, the deterministic algorithmic module receives parameters from the neural network module, supervises the parameters, and provided the parameters are within predetermined deterministic boundaries, controls IPG 20 to deliver DBS therapy responsive to the neural network module.

Figure 4:
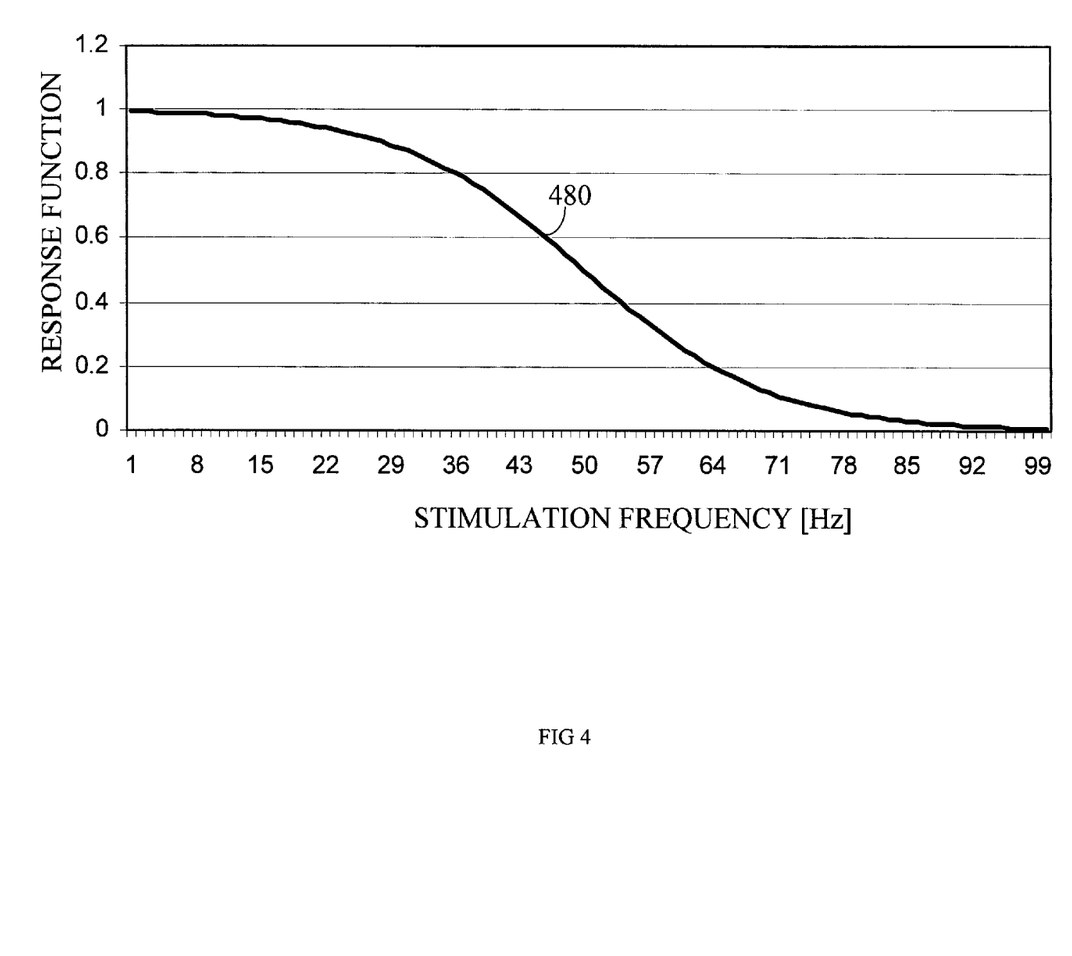
FIG. 4 illustrates an exemplary embodiment of an example of a response function calculated from a sensor signal as a function of deep brain stimulation frequency.

FIG. 4 illustrates an example embodiment of a response function to be calculated from the output of physiological sensor 30 as a function of deep brain stimulation frequency in accordance with a principle of the current invention, wherein the x-axis represents stimulation frequency in Hz and the y-axis represents the response function. A sigmoid curve 480 is exhibited since with an absence of deep brain stimulation the response function exhibits maximal values related for example to a mechanical body motion sensor embodiment of physiological sensor 30, i.e. with a zero stimulation frequency a maximal amount of uncontrolled movement is experienced. With increased stimulation frequency a reduced amount of uncontrolled movement of the patient occurs. With too strong stimulation the function remains low, however un-desired side effects may occur with too high stimulation frequency, hence the RL scheme traces the sigmoid inflection point to develop the ideal improvement without excess stimulation.

The main deviation from the I&F neurons learning scheme for an adaptive CRT cardiac pacemaker device mentioned above is the characteristic of the response function received from physiological sensor 30 that is used as the reinforcement signal for a synaptic weights adjustments learning scheme. With DBS, the sensor signal feedback function may exhibit a sigmoid curve and the optimal stimulation frequency in this case is correlated with the inflection point of the sigmoid curve.

Figure 5:
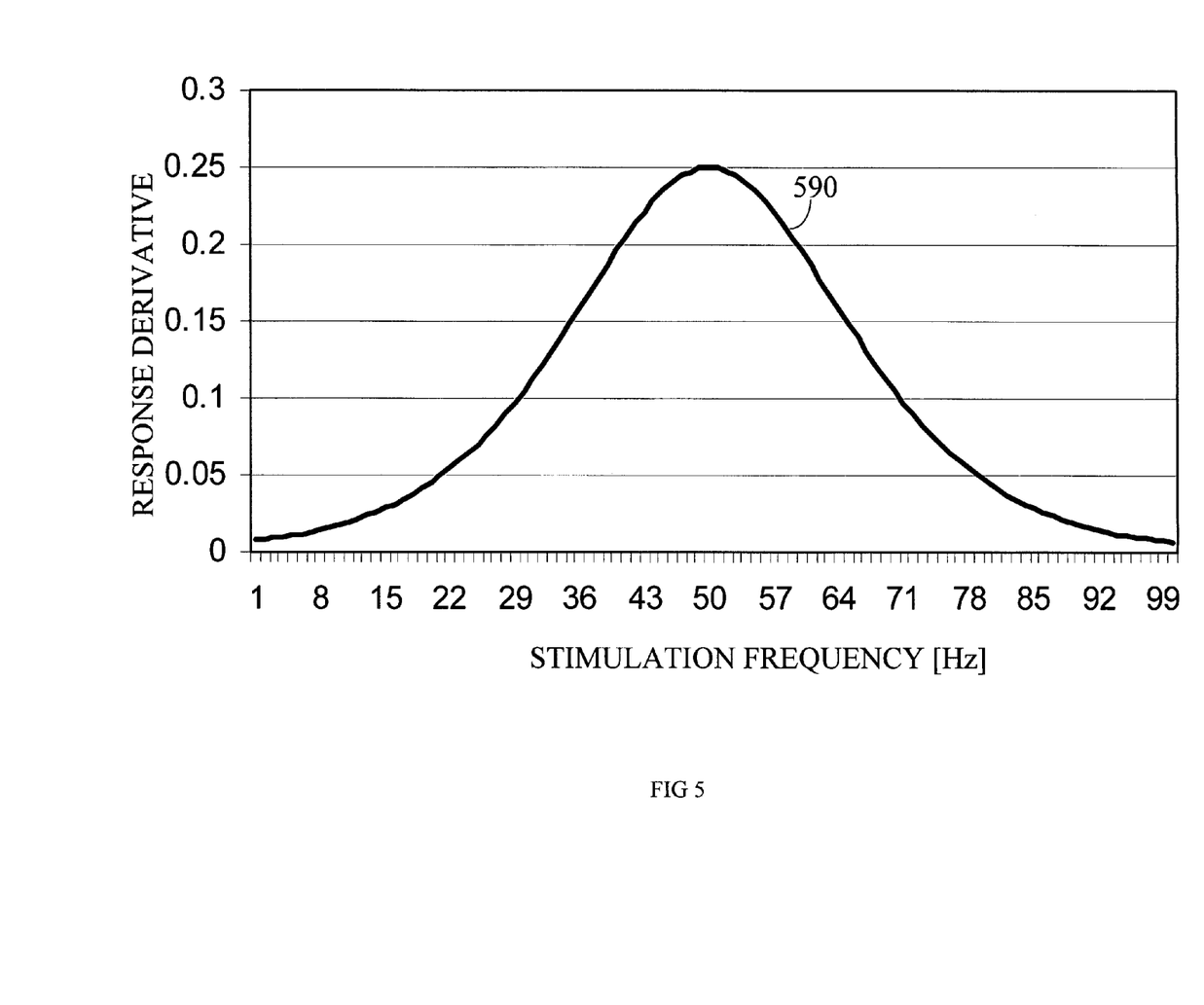
FIG. 5 illustrates an exemplary embodiment of the absolute value of a response function derivative of FIG. 4 as a function of deep brain stimulation frequency.

FIG. 5 illustrates the absolute value of a response function derivative of FIG. 4 as a function of deep brain stimulation frequency in accordance with a principle of the present embodiments, wherein the x-axis represents stimulation frequency in Hz and the y-axis represents the response function. The sigmoid derivative 590, shows a bell curve with a maximum absolute value corresponding to the inflection point of sigmoid curve 480 of FIG. 4 and hence the I&F neurons learning scheme presented for cardiac pacemakers for a bell curve feedback function can be implemented for DBS with the derivative of the function extracted from physiological sensor 30.

FIGS. 4 and 5 illustrate a response function as a function of the stimulation frequency, $\omega$, only as an example and other stimulation parameters such as the specific electrode selected dynamically from the optional multi-electrode DBS lead, P, can be used as optimization parameter of the QL scheme. Switching the stimulation delivery electrode will generate a different response curve since the DBS targets, the Globus Pallidum Internae or the subthalamic nucleus, are small and local targets, and changing the stimulation electrode by 1 to 10 mm or more along the multi-electrode lead will be significant. In an embodiment of the present invention the best response curve, with a maximal derivative value for example as shown in FIG. 5, will be used to select the preferred fixed delivery electrode. In another embodiment of the present invention the multi-electrode lead will be used as another optimization parameter that the QL scheme will vary dynamically as part of the learning scheme.

Figure 6:
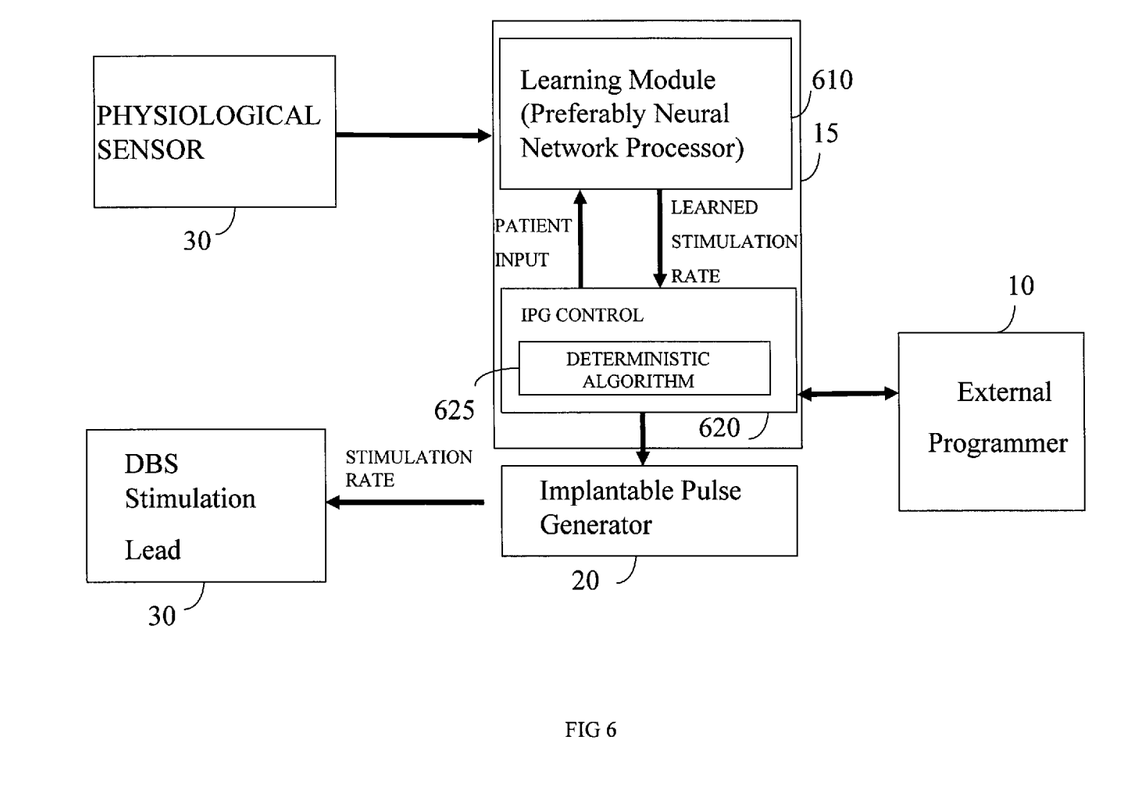
FIG. 6 illustrates an exemplary embodiment of a high level block diagram of the adaptive control system of FIG. 1, implemented as a neural network processor that performs dynamic optimization of stimulation parameters, solution of Q Learning recursive formula, pattern recognition and operation in four states with built in preference for the adaptive QL state.

FIG. 6 illustrates a high level block diagram of an exemplary embodiment of an adaptive control system 15 of FIG. 1, implemented as a learning module 610, preferably comprising a neural network processor, that performs dynamic optimization of stimulation parameters, solution of Watkins and Dayan QL formula, pattern recognition and operation in four states with built in preference. Adaptive control system 15 comprises: learning module 610, preferably comprising a neural network processor; and IPG control 620, comprising deterministic algorithmic module 625. FIG. 6 further illustrates: physiological sensor 30, whose output is received by learning module 610; external programmer 10 in bidirectional communication with IPG control 620; IPG 20 responsive to an output of IPG control 620; and DBS lead 40, preferably comprising a plurality of electrodes, responsive to IPG 20. Learning module 610 receives input from external programmer 10, via IPG control 620, of settings for IPG control 620, and outputs a learned stimulation rate to IPG control 620. IPG control 620 is operative, responsive to the state of learning module 610 to operate IPG 20 responsive to one of inputs from external programmer 10 and the learned stimulation rate output by learning module 610.

In particular, learning module 610 performs a machine learning algorithm, the I&F neurons learning scheme mentioned above and Watkins and Dayan QL learning scheme, to find the optimal stimulation frequency responsive to physiological sensor 30. Learning module 610 further uses a temporal pattern recognition sigmoid neural network to associate temporal patterns received from physiological sensor 30, which represents a condition of the patient, with the learned optimal frequency stimulation in adaptive GRL state 360. Learning module 610 further operates in four operational modes as shown in FIG. 3.

In particular, in non-adaptive state 350, learning module 610 learns the stimulation parameters programmed by the clinician via external programmer 10, received via IPG control 620. When the spiking learning module 610 learning task converges, learning module 610 switches to adaptive GA state 360 and performs a systematic trial and error GA scheme using the derivative of a sigmoid curve as the feedback for optimizing the stimulation frequency and/or other stimulation parameters. In adaptive GA state 360 the stimulation frequency can change from the programmed value of the clinician, however if any pre-defined failure occurs learning module 610 switches back to non-adaptive state 350 as a fallback safety state.

Learning module 610 further learns to associate the temporal pattern received from physiological sensor 30 with the learned optimal stimulation parameters programmed by the clinician via external programmer 10. When the learning module 610 learning task converges, i.e. when the temporal pattern neural network output is consonant within predetermined parameters with the output of the spiking neural network, a switch to adaptive QL state 370 occurs. Temporal patterns received from physiological sensor 30, preferably comprising at least one of a brain activity sensor and a mechanical motion sensor, represent patient conditions such as sleep, rest or exercise, and allow the system to deliver the optimal stimulation frequency for each patient condition in the adaptive QL state 370.

IPG control unit 620 manages learning module 610 and via deterministic algorithmic module 625 supervises learned parameters to ensure that they are within a preprogrammed maximum range. IPG control unit 620 further performs bidirectional communication with external programmer 10, and operates IPG 20 to perform stimulation. Deterministic algorithmic module 625 of IPG control 620 receives parameters from learning module 610, and provided the parameters are within predetermined deterministic boundaries, controls IPG 20 to deliver DBS therapy responsive to learning module 610.

Learning module 610 exhibits a built-in priority to operate in adaptive QL state 370. Transition to lower priority states occurs in the event of a failure to detect an incoming temporal pattern, a clinician override received via external programmer 10 of the stimulation frequency delivered, or any other predefined failure condition.

Figure 7:
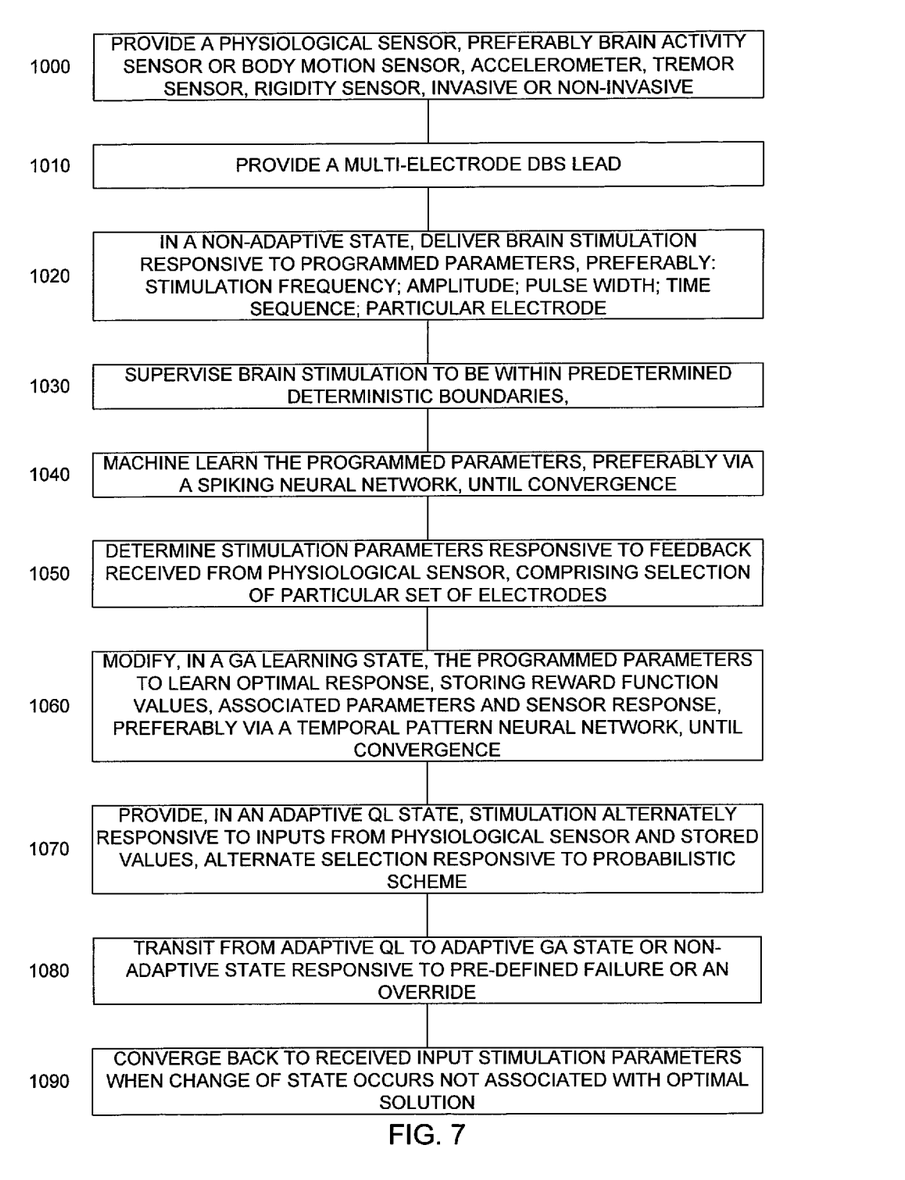
FIG. 7 illustrates a high level flow chart of an exemplary embodiment of a method of providing brain stimulation.

FIG. 7 illustrates a high level flow chart of an exemplary embodiment of a method of providing brain stimulation, preferably provided by adaptive control system 15. In stage 1000, a physiological sensor is provided, such as physiological sensor 30. Preferably the physiological sensor is at least one of a brain activity sensor and a body motion sensor, the motion sensor preferably comprising at least one of an accelerometer, tremor sensor and a rigidity sensor. In one embodiment the physiological sensor is invasive, and in another embodiment the physiological sensor is non-invasive. In stage 1010 a multi-electrode DBS lead is provided in contact with a subject.

In stage 1020, in a non-adaptive state, such as non-adaptive state 350, brain stimulation is delivered responsive to pre-programmed parameters. Preferably, the parameters comprise one or more of stimulation frequency, amplitude, pulse width, time sequence, and particular electrode, or electrodes, of the provided multi-electrode DBS lead of stage 1010.

In stage 1030, brain stimulation is supervised to ensure that stimulation delivered is within predetermined deterministic boundaries. In the event that the predetermined deterministic boundaries are exceeded, the stimulation parameters are constrained to not exceed the predetermined deterministic boundaries prior to actual stimulation. In stage 1040, the programmed parameters, and the response thereto is machine learned, preferably via a spiking neural network, such as learning module 610, until convergence of the machine learning is achieved.

In stage 1050 stimulation parameters are determined responsive to feedback received from the provided physiological sensor of stage 1000. The determined stimulation parameters particularly comprise selection of a particular set of electrodes of the provided multi-electrode DBS lead of stage 1010.

In greater detail, in stage 1060, in a GA learning state, such as GA learning state 360, the programmed parameters of stage 1020 are modified to learn the optimal response. A reward function, such as that described in relation to EQ. 1, is stored associated with the stimulation parameters and resultant output from the provided physiological sensor of stage 1000. Preferably, the modifying of parameters is performed by a temporal pattern neural network until convergence. In an exemplary embodiment convergence is defined as the output of the temporal pattern neural network being consonant within predetermined parameters with the output of the spiking neural network of stage 1040.

In stage 1070, responsive to the convergence of stage 1060, adaptive QL state, such as QL state 370, is transitioned to. In the adaptive QL state, DBS is alternately provided responsive to inputs from the physiologic sensor of stage 1000 and the stored values of stage 1060, the alternate selection performed responsive to a probabilistic scheme, as described above.

In stage 1080, the adaptive QL state of stage 1070 is exited in favor of the adaptive GA state of stage 1060 or the non-adaptive state of stage 1020 responsive to a pre-defined failure condition or an override received from an operator. In stage 1090, in the event that a change of state occurs to a state which is not associated with the optimal solution described above, the non-adaptive state of stage 1020 is transited to.

One advantage of the closed loop DBS control system described above is that preferably optimal lead positioning during brain surgery can be systematically used to validate the response to stimulation using a responder curve.

Another advantage of the closed loop DBS control system described above is that preferably convergence to optimal stimulation parameters is guaranteed mathematically by Watkins and Dayan online Q Learning scheme proof.

Another advantage of the closed loop DBS control system described above is that preferably whenever a new condition is detected, not recognized by the temporal pattern recognition network, the system automatically switches to lower priority state and when convergence again occurs the adaptive control system returns to adaptive GRL DBS state 370 due to the built-in preference described above.

Another advantage of the closed loop DBS control system described above is that preferably undesired side effects due to brain stimulation may be reduced by the adaptive control system that learns to deliver stimulation frequency responsive to a feedback function received from physiological sensor 30.

Advantageously, the closed loop DBS control system preferably overcomes the difficulties of sub-optimal DBS therapy due to both sub-optimal DBS lead positioning and the lack of systematic patient follow-up routine aimed at optimizing the DBS device stimulation parameters manually after a DBS lead is implanted.

Advantageously, the closed loop DBS control system is preferably tailored to the patient, will allow optimal stimulation at different patient conditions, and have a safety fallback state, which is the non-adaptive DBS state with the programmed stimulation parameters.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

I claim:

1. A closed loop Deep Brain Stimulation (DBS) system comprising:
a physiological sensor, said physiological sensor comprising at least one of a brain activity sensor and a mechanical body motion sensor;
an adaptive control system in communication with said physiological sensor; and
an implantable pulse generator (IPG), said IPG arranged to provide pulses selectively to one or more electrodes of a multi-electrode DBS lead responsive to stimulation parameters provided by said adaptive control system,
said adaptive control system comprising:
a learning module arranged to determine stimulation parameters to be output to said IPG responsive to feedback received from said physiological sensor wherein said stimulation parameters comprise a selection of a particular set of said one or more electrodes of said multi-electrode DBS lead; and
a deterministic algorithmic module arranged to maintain safety limits for determined stimulation parameters provided to said IPG,
wherein said adaptive control system is arranged to operate in a plurality of states, the states comprising:
a non-adaptive state wherein said adaptive control system controls said IPG to deliver stimulation in accordance with received input stimulation parameters;
an adaptive gradient ascent (GA) learning state wherein said input stimulation parameters are modified by said adaptive control system and optimal parameters for varying patient conditions are learned responsive to feedback received from said physiological sensor, said learning comprising storing reward function values responsive to said modified stimulation parameters and resultant inputs from said physiological sensor in a Q-learning (QL) look up table; and
an adaptive QL state in which said adaptive control system operates said IPG alternately responsive to inputs from said physiologic sensor and inputs stored in said QL look up table, said alternate selection responsive to a probabilistic scheme.

2. The closed loop DBS system of claim 1, wherein said stimulation parameters further comprise at least one of a stimulation frequency, amplitude, a pulse width, and time sequences.

3. The closed loop DBS system according to claim 1, further comprising an external programmer in communication with said adaptive control system, said received input stimulation parameters provided via said external programmer.

4. The closed loop DBS system according to claim 1, wherein said physiological sensor comprises at least one of an accelerometer, a tremor sensor and a rigidity sensor.

5. The closed loop DBS system according to claim 1, wherein said physiological sensor is invasive.

6. The closed loop DBS system according to claim 1, wherein said physiological sensor is non-invasive.

7. The closed loop DBS system according to claim 1, wherein said adaptive control system comprises a neural network type processor.

8. The closed loop DBS system according to claim 1, wherein said adaptive control system further comprises:
an adaptive FAIL QL state in which a pattern recognition sigmoid neural network is operative to converge back to the received input stimulation parameters when a change of state occurs and the pattern recognition networks fails to associate the new pattern with an optimal solution.

9. The closed loop DBS system according claim 8, wherein said adaptive control system exhibits a built in priority to operate in said adaptive QL state.

10. The closed loop DBS system according to claim 9, wherein said adaptive control system transits from said adaptive QL state to one of said adaptive GA learning state and non-adaptive state responsive to one of:
a pre-defined failure; and
an override input.

11. A method for deep brain stimulation (DBS) delivered to a patient in a closed loop system, said method comprising:
providing a physiological sensor;
providing a multi-electrode DBS lead;
determining stimulation parameters to be provided via said provided multi-electrode DBS lead responsive to feedback received from said provided physiological sensor wherein said stimulation parameters comprise a selection of a particular set of said one or more electrodes of said provided multi-electrode DBS lead; and
maintaining safety limits for said stimulation parameters provided to said multi-electrode DBS lead,
wherein said determining stimulation parameters comprises:
delivering brain stimulation via said provided multi-electrode DBS lead according to programmed stimulation parameters;
machine learning the programmed stimulation parameters;
switching to an adaptive gradient ascent (GA) learning state when the machine learning converges;
modifying the programmed stimulation parameters thereby learning optimal stimulation parameters responsive to feedback from said provided physiological sensor;
storing reward function values responsive to said modified stimulation parameters and resultant inputs from said physiological sensor in a Q-learning (QL) look up table; and
in the event that said learning optimal stimulation parameters converges within predetermined parameters, switching to an adaptive QL state in which brain stimulation is provided via said provided multi-electrode DBS lead alternately responsive to inputs from said physiologic sensor and inputs stored in said QL look up table, said alternate selection responsive to a probabilistic scheme.

12. The method of claim 11, further comprising receiving said programmed stimulation parameters, said programmed stimulation parameters comprising at least one of a stimulation frequency, amplitude, a pulse width, a particular electrode of said multi-electrode DBS lead and a time sequence.

13. The method of claim 12, further comprising:
converging back to the received programmed stimulation parameters when a change of state occurs which is not associated with the optimal stimulation parameters.

14. The method of claim 13, wherein the method exhibits a built in priority to operate in said adaptive QL state.

15. The method of claim 13, further comprising transiting from said adaptive QL state to one of said adaptive GA state and non-adaptive state responsive to one of:
a pre-defined failure; and
an override input.

16. The method of claim 11, wherein said provided physiological sensor comprises at least one of a brain activity sensor and a mechanical body motion sensor.

17. The method of claim 11, wherein said provided physiological sensor comprises at least one of an accelerometer, a tremor sensor and a rigidity sensor.

* * * * *